United States Patent
Misu et al.

(10) Patent No.: US 6,245,935 B1
(45) Date of Patent: Jun. 12, 2001

(54) METHOD FOR PRODUCING ISOCYANATOALKYL (METH)ACRYLATE

(75) Inventors: Naoaki Misu, Fukushima; Shinya Matsuhira, Kanagawa; Muneyo Kihara; Yutaka Ohnishi, both of Kanagawa, all of (JP)

(73) Assignee: Showa Denko Kabushiki Kaisha, Tokyo (JP)

(*) Notice: Subject to any disclaimer, the term of this patent is extended or adjusted under 35 U.S.C. 154(b) by 0 days.

(21) Appl. No.: 09/245,707

(22) Filed: Feb. 8, 1999

Related U.S. Application Data
(60) Provisional application No. 60/101,527, filed on Sep. 23, 1998.

(30) Foreign Application Priority Data

Feb. 6, 1998 (JP) .................................................. 10-025493

(51) Int. Cl.$^7$ ..................................................... C07C 67/48
(52) U.S. Cl. ............................................................. 560/218
(58) Field of Search ............................................... 560/218

(56) References Cited

U.S. PATENT DOCUMENTS 4,310,688 * 1/1982 Mendoza .

OTHER PUBLICATIONS

Chem. Abst 119: 73293 (Jpn 05058982 Sep. 3, 1993).*

* cited by examiner

*Primary Examiner*—Paul J. Killos
(74) *Attorney, Agent, or Firm*—Sughrue, Mion, Zinn, Macpeak & Seas, PLLC

(57) ABSTRACT

A method for producing an isocyanatoalkyl (meth)acrylate substantially free of hydrolyzable chloride, comprising adding an amine and/or an imidazole and an epoxy group-containing compound and then purifying by distillation the isocyanatoalkyl (meth)acrylate until a 2-chloropropionic acid isocyanatoalkyl ester of an isocyanatoalkyl acrylate or a 2-methyl-2-chloropropionic acid isocyanatoalkyl ester of an isocyanatoalkyl methacrylate is substantially eliminated.

8 Claims, No Drawings

METHOD FOR PRODUCING ISOCYANATOALKYL (METH)ACRYLATE

CROSS REFERENCE TO RELATED APPLICATIONS

This application is an application filed under 35 U.S.C. §111(a) claiming benefit pursuant to 35 U.S.C. §119(e)(i) of the filing date of the Provisional Application 60/101,527 filed Sep. 23, 1998 pursuant to 35 U.S.C. §111(b).

BACKGROUND OF THE INVENTION

1. Field of the Invention

The present invention relates to an isocyanatoalkyl (meth) acrylate substantially free of hydrolyzable chloride, which is obtained by removing hydrolyzable chloride from an isocyanatoalkyl (meth)acrylate containing hydrolyzable chloride, and a production method therefor. The isocyanatoalkyl (meth)acrylate substantially free of hydrolyzable chloride provided by the present invention is useful particularly as a material or raw material of a photoresist and the like for electronic materials.

In the present invention, unless otherwise indicated, the term "(meth)acrylate" includes acrylate and methacrylate.

2. Description of Related Art

The isocyanatoalkyl (meth)acrylate represented by 2-isocyanatoethyl methacrylate is a compound containing both an isocyanato group highly reactive with a compound having an active hydrogen, for example, a compound having a substituent such as a hydroxyl group or a primary or secondary amino group and a vinyl polymerizable carbon-carbon double bond within the same molecule. This is an industrially very useful compound and it is used in many applications such as paints, coating materials, adhesives, photoresists, dental materials and magnetic recording materials. This compound is produced using phosgene as described in U.S. Pat. No. 2,821,544 and JP-A-54-5921 (The term "JP-A" as used herein means an "unexamined published Japanese patent application") and in general, contains an impurity called "hydrolyzable chloride". (In the present invention, unless otherwise indicated, the term "hydrolyzable chloride" means chlorine in a chlorine-containing compound which is hydrolyzable.) A representative example of the compound is a chlorine-containing compound such as (meth)acryloyloxyalkylcarbamoyl chloride present in a product containing the desired object in the production of an isocyanatoalkyl (meth)acrylate.

If a urethane acrylate or the like is produced using an isocyanatoalkyl (meth)acrylate containing a hydrolyzable chloride, the hydrolyzable chloride acts as a catalyst poison. Moreover, the chlorine compound mixed with a product adversely affects weatherability and corrosion resistance. In particular, the presence of hydrolyzable chloride may be fatal to the photoresist material for electronic equipment use.

Heretofore, various methods for reducing the hydrolyzable chloride in an isocyanato compound in general have been disclosed.

For example, JP-A-53-119823 discloses a method of mixing a hydrolyzable chloride-containing isocyanato compound with a fine alkali metal carbonate at a high temperature for a long period of time. JP-A-59-172450 discloses a method of adding a carboxylate of zinc and a hindered phenol-type antioxidant to a hydrolyzable chloride-containing isocyanato compound and subjecting the mixture to heat treatment and then distillation. U.S. Pat. No. 3,465,023 discloses a method of synthesizing an isocyanate in a water-insoluble solvent and then rinsing it with an aqueous sodium hydrogen carbonate solution; and German Patent 2,249,375 discloses a method of treating a hydrolyzable chloride-containing polymethylenepolyphenyl isocyanate with an epoxy compound.

Furthermore, as a method which does not use chemicals such as an alkali metal carbonate described above, JP-A-61-161250 discloses a method of vaporizing a hydrolyzable chloride-containing isocyanato compound and then purifying the isocyanato compound by condensation at a temperature of 70° C. or higher.

However, these methods cannot achieve satisfactory reduction of hydrolyzable chloride or have various problems to be solved in their industrial implementation. For example, according to the method of mixing a hydrolyzable chloride-containing isocyanato compound with an alkali metal carbonate at a high temperature described in JP-A-53-119823, the isocyanato compound and the carbonate after treatment are difficult to separate, which gives rise to inevitable generation of loss. The method involving rinsing with an aqueous sodium hydrogen carbonate solution described in U.S. Pat. No. 3,465,023 is disadvantageous in that white insoluble matters precipitate at the boundary between an organic phase and an aqueous phase and this renders the subsequent separation operation cumbersome or causes staining of the apparatus. Furthermore, these methods have the concern that isocyanato compound is contaminated with sodium ion. Even if the sodium ion content is on the order of ppm, a serious problem arises in using the isocyanato compound in electronic materials.

Particularly, in purifying an isocyanato compound having a carbon-carbon double bond, the hydrolyzable chloride content must be effectively reduced while preventing a polymerization reaction between the isocyanato compounds with each other, However, satisfactory results cannot be achieved by the above-described methods.

U.S. Pat. No. 4,310,688 discloses a method of treating a methylene chloride solution of isocyanatoethyl methacrylate containing 0.21% of hydrolyzable chloride with a vicinal epoxy group-containing compound (e.g., 1,2-butylene oxide) to thereby reduce the hydrolyzable chloride content to 0.05%. However, by this method, the hydrolyzable chloride content can be reduced at most only to hundreds of ppm and the purified isocyanato compound obtained does not have sufficient properties for use in electronic materials.

In order to solve these problems in conventional techniques, the present inventors have proposed a method of reducing the hydrolyzable chloride content in an isocyanato compound by treating it with an epoxy compound in the presence of an amine (JP-A-9-323958). This method is an excellent method but still fails to achieve complete removal of hydrolyzable chloride.

On the other hand, a method of producing an isocyanato compound without using phosgene has also been studied. For isocyanatoalkyl (meth)acrylate, a method using thermal decomposition of a urethane compound has been proposed (see, U.S. Pat. No. 2,718,516, JP-A-62-10053, JP-A-62195354, JP-A-5-186414, JP-A-5-186415 and JP-A-6-263712). This method comprises a step of thermal decomposition at a high temperature and since the isocyanatoalkyl (meth)acrylate is very readily polymerized, the yield is not satisfactory by any means in view of profitability.

SUMMARY OF THE INVENTION

The present invention has been made to solve the problems in conventional techniques.

An object of the present invention is to provide a method for industrially producing an isocyanatoalkyl (meth)acrylate substantially free of hydrolyzable chloride from an isocyanatoalkyl (meth)acrylate produced using phosgene.

As a result of extensive investigations to attain the above-described object, the present inventors have accomplished the present invention.

More specifically, the present invention provides the following embodiments.

(1) a method for producing an isocyanatoalkyl (meth) acrylate substantially free of hydrolyzable chloride, comprising purifying an isocyanatoalkyl (meth) acrylate containing a hydrolyzable chloride until a 2-chloropropionic acid isocyanatoalkyl ester of an isocyanatoalkyl acrylate or a 2-methyl-2-chloropropionic acid isocyanatoalkyl ester of an isocyanatoalkyl methacrylate is substantially eliminated;

(2) the production method as described in (1) above, wherein the isocyanatoalkyl (meth)acrylate used in the purification step has a hydrolyzable chloride content of 100 ppm or less;

(3) the production method as described (2) above, wherein the purification is performed after a step of treating an isocyanatoalkyl (meth)acrylate containing a hydrolyzable chloride with an epoxy group-containing compound and an amine and/or an imidazole to reduce the content of the hydrolyzable chloride in the isocyanatoalkyl (meth)acrylate to 100 ppm or less;

(4) the production method as described in (1) to (3) above, wherein the purification is performed by distillation at a distillation temperature of less than 100° C. under reduced pressure in the presence of a polymerization inhibitor;

(5) the production method as described in (3) or (4) above, wherein the amine is a trialkylamine (with the alkyl group having from 4 to 15 carbon atoms) or a compound represented by the following formula (I)

$$H_2N-(CH_2CH_2NH)_n-H \qquad (I)$$

wherein n represents an integer of 2 or more, and the imidazole is a 2-alkyl4-alkylimidazole with the alkyl groups each independently having from 1 to 3 carbon atoms;

(6) the production method as described in (3) to (5) above, wherein the treatment is performed using an epoxy group-containing compound in an amount of from 1 to 10 molar times and an amine and/or an imidazole in an amount of from 0.2 to 2 molar times the content of the hydrolyzable chloride;

(7) the production method as described in (1) to (6) above, wherein the isocyanatoalkyl (meth)acrylate is 2-isocyanatoethyl methacrylate;

(8) an isocyanatoalkyl (meth)acrylate substantially free of hydrolyzable chloride, comprising the isocyanatoalkyl acrylate containing substantially no 2-chloropropionic acid isocyanatoalkyl ester or the isocyanatoalkyl methacrylate containing substantially no 2-methyl-2-chloropropionic acid isocyanatoalkyl ester; and (9) 2-isocyanatoethyl methacrylate substantially free of hydrolyzable chloride, which contains substantially no 2-methyl-2-chloropropionic acid 2-isocyanatoethyl ester.

DETAILED DESCRIPTION OF THE INVENTION

In the purification process in the production method of an isocyanatoalkyl (meth)acrylate substantially free of hydrolyzable chloride according to the present invention, the content of hydrolyzable chloride in a product to be purified is not particularly limited. However, in view of the profitability of the process, it is usually advantageous to use an isocyanatoalkyl (meth)acrylate having a hydrolyzable chloride content of 1,000 ppm or less, preferably 100 ppm or less. For example, an isocyanatoalkyl (meth)acrylate containing hydrolyzable chloride is preferably treated with an epoxy compound in the presence of an amine and/or an imidazole to reduce the hydrolyzable chloride content to 100 ppm or less before it is used in the purification step.

The purification process of the present invention is characterized in that the purification is performed, for example, by vacuum distillation until a 2-chloropropionic acid isocyanatoalkyl ester or a 2-methyl-2-chloropropionic acid isocyanatoalkyl ester as one of the by-products in the synthesis of an isocyanatoalkyl (meth)acrylate is substantially eliminated to thereby obtain an isocyanatoalkyl (meth)acrylate substantially free of hydrolyzable chloride.

In the purification of isocyanatoalkyl (meth)acrylate according to the present invention, crude isocyanatoalkyl (meth)acrylate is treated with an epoxy compound in the presence of an amine and/or an imidazole as a catalyst and then purified under mild conditions. Accordingly, an isocyanatoalkyl (meth)acrylate substantially free of hydrolyzable chloride can be efficiently obtained in a good yield without having any adverse effect on the quality of the isocyanatoalkyl (meth)acrylate. Furthermore, this purification method can be easily implemented in industry.

The present invention is described further in detail below.

The amount of the hydrolyzable chloride according to the present invention is expressed as a value of chlorine obtained by an analysis method described in JIS K 1556 (Tolylene Diisocyanato Test Method) or an analysis method equivalent thereto in principle. In general, hydrolyzable chloride determined by such a method is presumed to be a mixture of a plurality of chlorine compounds rather than a specific compound. For example, assuming that an isocyanatoalkyl (meth)acrylate is R—NCO, chlorine compounds in the form of R—NH—COCl, R—NCl$_2$ or R—N=C (Cl)—R'•HCl (wherein R' represents a vinyl group or an isopropenyl group) are considered to be present, however, details are not known. Furthermore, the hydrolyzable chloride is a mixture of compounds relatively easy to remove or difficult to remove and this has been an obstacle to the production (purification) of an isocyanatoalkyl (meth) acrylate substantially free of hydrolyzable chloride.

The analysis method of the hydrolyzable chloride for use in the present invention and used in the Examples described later is outlined below. Into a 500 ml-volume short-neck Kjeldahl flask, 100 ml of methyl alcohol, 100 ml of water and 10 ml of a sample (when the hydrolyzable chloride content is small, both methanol and sample are increased) are charged, and a reflux condenser is fixed thereto. The contents are heated under reflux for 30 minutes, then cooled to room temperature and subjected to potentiometric titration using a N/100 silver nitrate solution.

The isocyanatoalkyl (meth)acrylate provided by the present invention is a compound represented by formula (II)

$$CH_2=C(R_1)-COO-R_2-NCO \qquad (II)$$

wherein $R_1$ represents a hydrogen atom or a methyl group and $R_2$ represents an alkylene group, preferably a compound where $R_2$ is an alkylene group having from 2 to 6 carbon atoms, more preferably in view of reactivity, easy availability and good handleability, a compound where $R_2$ is an ethylene group (—CH$_2$CH$_2$—), namely, 2-isocyanatoethyl (meth)acrylate, and still more preferably 2-isocyanatoethyl methacrylate.

In the present invention, the amount of hydrolyzable chloride present in an isocyanatoalkyl (meth)acrylate to be treated in the step previous to the purification step is suitably 10,000 ppm or less, preferably 3,000 ppm or less. When the amount of hydrolyzable chloride initially present exceeds this range, the amount of hydrolyzable chloride is preferably reduced by another method. Examples of these other methods include various methods such as a method of adding an epoxy compound and performing vacuum distillation, a method of refluxing the isocyanatoalkyl (meth)acrylate while blowing thereinto an inert gas such as nitrogen, and a method of adding a tertiary amine such as triethylamine in an amount slightly smaller than that of hydrolyzable chloride and separating generated crystals of tertiary amine hydrochloride salt by filtration. An appropriate method may be selected depending on the situation.

To an isocyanatoalkyl (meth)acrylate containing hydrolyzable chloride thus reduced to a certain level, an epoxy group-containing compound (hereinafter sometimes simply referred to as an "epoxy compound") and an amine and/or an imidazole are added and reacted with the hydrolyzable chloride.

The epoxy compound for use in the present invention preferably presents a larger difference in the boiling point between the epoxy compound and the isocyanatoalkyl (meth)acrylate of the present invention, so that a very conventional distillation method can be used for the separation and purification which will be described later. The difference in the boiling point is suitably 5° C. or more, preferably 20° C. or more.

The epoxy compound is not particularly limited as far as it has an epoxy group within the molecule and does not additionally contain any active hydrogen reactive with an isocyanato group. Examples thereof include aliphatic or alicyclic alkylene oxide, epoxidized fatty acid ester and epoxidized triglyceride.

Examples of suitable aliphatic alkylene oxides include propylene oxide, butylene oxide and hexene oxide. Examples of suitable alicyclic alkylene oxides include cyclohexene oxide, cyclopentene oxide and these oxides having a substituent.

Examples of the epoxidized fatty acid ester include those having a molecular weight of approximately from 300 to 500, such as epoxidized alkyl stearate.

Examples of suitable epoxidized triglycerides include those (molecular weight: approximately from 500 to 1,500, iodine value: from 2 to 14, oxirane oxygen amount: approximately from 2 to 15%) obtained by oxidizing a fat and oil such as soybean oil or cotton seed oil with an aqueous solution of hydrogen peroxide in a solvent such as acetic acid or formic acid in the presence of an acid catalyst.

The oxirane oxygen amount in the epoxy compound is determined by reacting an epoxy compound with a known amount of hydrogen chloride, titrating excess hydrogen chloride with an alkali standard solution and comparing the titer with the blank value.

In the present invention, these epoxy compounds can be used individually or as a combination of two or more thereof.

Of the above-described epoxy compounds, epoxidized fatty acid esters and epoxidized triglyceride are preferred.

The epoxy compound is suitably used in an amount of from 1 to 5 equivalents, preferably 1.5 to 3 equivalent, per equivalent of the hydrolyzable chloride (1 mol of chlorine atom). If the amount of the epoxidized compound is less than 1 equivalent per equivalent of the hydrolyzable chloride, the hydrolyzable chloride cannot be efficiently and satisfactorily removed, and the effect is small, whereas even if the amount exceeds 5 equivalents, the effect by the addition is not elevated any more and this is uneconomical.

The equivalent number of the epoxy compound is calculated as the (number of oxygen atom (oxirane oxygen) constituting the epoxy group×number of moles) present in the epoxy group.

The amine and/or imidazole for use in the present invention may be a primary amine, a secondary amine or a tertiary amine and may also be chained, branched or cyclic amine. The chained amine may have an alicyclic or aromacyclic structure and may have one amino group or a plurality of amino groups. However, preferably one or more compounds are selected from triethylenetetramine, triheptylamine, trioctylamine, trinonylamine, tridecylamine, 1,4-diazabicyclo[2.2.2]octane, imidazole, 2-ethyl-4-methylimidazole, 2,4-dimethylimidazole, 2-methylimidazole, 2,4-diethylimidazole and 1-benzyl-2-methylimidazole, more preferably one or more compounds are selected from triethylenetetramine, trioctylamine and 2-ethyl-4-methylimidazole.

The amine and/or imidazole is suitably used in an amount of generally from 0.2 to 2.0 equivalents, preferably from 0.3 to 1.0 equivalent, per equivalent of the hydrolyzable chloride. If the amount of the amine and/or imidazole is less than 0.2 equivalent, almost no effect is provided by the addition, whereas if the amount exceeds 2 equivalents, the solution becomes excessively basic and this gives rise to disadvantageous side reactions such as polymerization of the isocyanato group. Furthermore, if the amount of the primary or secondary amine increases, the reaction with an isocyanatoalkyl (meth)acrylate cannot be neglected any more but it results in not only reduction of the yield but also gelation occurs.

The equivalent number of the amine and/or imidazole is calculated by the number of nitrogen atom×number of moles. (For example, in the case of an imidazole having two nitrogen atoms, 1 mol corresponds to 2 equivalents.)

Thus, hydrolyzable chloride and an epoxy compound are reacted in the presence of an amine and/or imidazole at from 30 to 100° C., preferably from 40 to 80° C. The reaction time does not greatly affect the effect and is not particularly limited but it is appropriately on the order of from 30 minutes to 3 hours.

Thereafter, if desired, isocyanatoalkyl (meth)acrylate is separated by simple distillation or by extraction or a like method. As a result, an isocyanatoalkyl (meth)acrylate having a hydrolyzable chloride content of 1,000 ppm or less, preferably 100 ppm or less, more preferably 50 ppm or less, can be obtained.

Subsequently, the isocyanatoalkyl (meth)acrylate obtained is rectified in distillation equipment having a rectification tower and a refluxing apparatus. The rectification tower is not particularly limited, however, those having a pressure loss as small as possible, for example, a rectification tower packed with an appropriate packing, are preferred. The theoretical plate number of the rectification tower and the reflux ratio vary depending on the kind of the compound, the distillation pressure or the like and cannot be specifically set forth. However, the purification is performed by appropriately adjusting these conditions until a 2-chloropropionic acid isocyanatoalkyl ester (in the case of an isocyanatoalkyl acrylate) or a 2-chloro-2-methylpropionic acid isocyanatoalkyl ester (in the case of an isocyanatoalkyl methacrylate) as one of by-products is substantially not detected by gas chromatography. The 2-chloropropionic acid isocyanatoalkyl ester or 2-chloro-2-methylpropionic acid isocyanatoalkyl ester is not detected by the above-described analysis of hydrolyzable chloride and seems to have no relation, however, by removing these, an isocyanatoalkyl (meth)acrylate substantially free of hydrolyzable chloride can be obtained.

Although depending on the kind of the compound, the following detection conditions of gas chromatography are usually employed in case of 2-isocyanatoethyl methacrylate as a representative example.

Column: DB-1, manufactured by J&W Scientific inner diameter: 0.32 mm, length: 30 m, liquid phase film thickness: 1.0 $\mu$m Temperature:

column: 80° C. for an initial 8 minutes, then the temperature is elevated at 10° C./min, and the final temperature is 300° C.

injection: 200 to 300° C.

detector: 300° C.

Detector: flame ionization detector

Carrier gas: helium flow rate: column: 3 ml/min, split: 100 ml/min.

EXAMPLES

The present invention is described in greater detail below by referring to the Examples, however, the present invention is by no means limited to these Examples. Unless otherwise indicated, all parts, percentages and the like are by weight.

Example 1

To a 500 ml-volume glass-made reactor equipped with a distilling head (reflux ratio regulating), a thermometer, a stirrer and a heating bath, 300 g of 2isocyanatoethyl methacrylate (boiling point: 211 ° C.) having a hydrolyzable chloride content of 381 ppm, 1.7 g of an epoxidized fat and oil-type plasticizer (molecular weight: about 1,000, iodine value: 7) having an oxirane oxygen content of 6.1%, 0.3 g of 2,6-di-tert-butyl-4-methylphenol and 0.11 g of triethylenetetramine (boiling point: 277.4° C.) were charged. The mixture was stirred at 60° C. for 2.5 hours and then distilled at about 1.3 kPa and 85° C. After the initial fraction reached 10% of the charge, the receiver was changed. Then, 220 g of purified 2-isocyanatoethyl methacrylate was obtained.

The hydrolyzable chloride in this fraction was analyzed by the method described above and found to be 29 ppm. The value of 2-chloro-2methylpropionic acid 2-isocyanatoethyl ester analyzed by gas chromatography equipped with a flame ionization detector was 265 ppm in terms of the ratio of peak area of the compound to the entire peak area derived from the sample (hereinafter referred to a "simple peak area ratio") on the chromatogram.

Thereafter, two glass columns each having an inner diameter size of 20 mm and a length of 30 cm and packed with 3 mm$\phi$ Dixon packing were connected in series and by using this as the rectification tower, 150 g of the purified 2-isocyanatoethyl methacrylate obtained above having added thereto 0.15 g of phenothiazine was distilled at about 0.7 kPa, a distillation temperature of 70° C. and a bottom temperature of 81° C.

When an initial fraction of 14.8 g was distilled, the receiver was changed and continuously, 53 g was distilled. This fraction was analyzed by gas chromatography but 2-chloro-2-methylpropionic acid 2-isocyanatoethyl ester was not detected. Also, the hydrolyzable chloride content was analyzed and found to be nil (detection limit: 1 ppm or less).

Comparative Example 1

The 2-isocyanatoethyl methacrylate containing 381 ppm of hydrolyzable chloride used in Example 1 was distilled in the same manner using the distillation equipment of Example 1 except for omitting the pre-treatment. When an initial fraction of 15 g was distilled, the receiver was changed and continuously 51 g was distilled. In the fraction obtained, 2-chloro-2-methylpropionic acid 2-isocyanatoethyl ester was not detected but hydrolyzable chloride content analyzed was found to be 124 ppm.

Comparative Example 2

The procedure of Example 1 was repeated except that one glass column of Example 1 was used as the distillation tower and the packing was changed to 6 mm$\phi$ Dixon packing.

In the distillate obtained, 0.01% in terms of a simple peak area ratio of 2-chloro-2-methylpropionic acid 2-isocyanatoethyl ester was detected and the hydrolyzable chloride content analyzed was found to be 16 ppm.

Example 2

The procedure of Example 1 was repeated except for using 2-isocyanatoethyl acrylate having a hydrolyzable chloride content of 460 ppm.

The distillate obtained was analyzed by gas chromatography but 2-chloropropionic acid 2-isocyanatoethyl ester was not detected. Further, the hydrolyzable chloride was found to be below the detection limit.

Example 3

The procedure of Example 1 was repeated except for using 2-isocyanatopropyl methacrylate having a hydrolyzable chloride content of 451 ppm. The distillate obtained was analyzed by gas chromatography but 2-chloro-2-methylpropionic acid 2-isocyanatopropyl ester was not detected. Further, the hydrolyzable chloride content was found to be below the detection limit.

According to the present invention, an isocyanatoalkyl (meth)acrylate substantially free of hydrolyzable chloride can be industrially produced. In particular, the isocyanatoalkyl (meth)acrylate produced can be used as a raw material of an active radiation curable resin or the like suitable for uses having a dislike to chlorine, such as electronic materials.

What is claimed is:

1. A method for producing an isocyanatoalkyl (meth) acrylate substantially free of hydrolyzable chloride, comprising (i) treating an isocyanatoalkyl (meth)acrylate containing a hydrolyzable chloride with an epoxy group-containing compound and an amine and/or an imidazole to reduce the content of the hydrolyzable chloride in the isocyanatoalkyl (meth)acrylate to 100 ppm or less and subsequently, (ii) purifying the isocyanatoalkyl (meth)acrylate containing hydrolyzable chloride until in case of an isocyanatoalkyl acrylate a 2-chloropropionic acid isocyanatoalkyl ester or in case of an isocyanatoalkyl methacrylate a 2-methyl-2chloropropionic acid isocyanatoalkyl ester is substantially eliminated.

2. The production method as claimed in claim 1, wherein the purification comprises distilling at a distillation temperature of less than 100° C. under reduced pressure in the presence of a polymerization inhibitor.

3. The production method as claimed in claim 1, wherein the amine is a trialkylamine with the alkyl moiety having from 4 to 15 carbon atoms or a compound represented by the following formula (I)

(I)

wherein n represents an integer of 2 or more; and the imidazole is a 2-alkyl-4-alkylimidazole with the alkyl groups each independently having from 1 to 3 carbon atoms.

4. The production method as claimed in claim 1, wherein the treating is performed using an epoxy group-containing compound in an amount of from 1 to 5 molar times and an amine and/or an imidazole in an amount of from 0.2 to 2 molar times the content of the hydrolyzable chloride.

5. The production method as claimed in claim 1, wherein the isocyanatoalkyl (meth)acrylate is 2-isocyanatoethyl methacrylate.

6. The production method as claimed in claim 2, wherein the isocyanatoalkyl (meth)acrylate is 2-isocyanatoethyl methacrylate.

7. The production method as claimed in claim 3, wherein the isocyanatoalkyl (meth)acrylate is 2-isocyanatoethyl methacrylate.

8. The production method as claimed in claim 4, wherein the isocyanatoalkyl (meth)acrylate is 2-isocyanatoethyl methacrylate.

* * * * *